US010258003B2

(12) United States Patent
Gibson

(10) Patent No.: US 10,258,003 B2
(45) Date of Patent: Apr. 16, 2019

(54) LETTUCE VARIETY 'PRO 1632'

(71) Applicant: PROGENY ADVANCED GENETICS, Salinas, CA (US)

(72) Inventor: George Darryn Gibson, Prunedale, CA (US)

(73) Assignee: Progeny Advanced Genetics, Salinas, CA (US)

( * ) Notice: Subject to any disclaimer, the term of this patent is extended or adjusted under 35 U.S.C. 154(b) by 0 days.

(21) Appl. No.: 15/454,971

(22) Filed: Mar. 9, 2017

(65) Prior Publication Data

US 2017/0258030 A1 Sep. 14, 2017

Related U.S. Application Data

(60) Provisional application No. 62/307,243, filed on Mar. 11, 2016.

(51) Int. Cl.
*A01H 5/12* (2018.01)
*A01H 6/14* (2018.01)

(52) U.S. Cl.
CPC ............. *A01H 5/12* (2013.01); *A01H 6/1472* (2018.05)

(58) Field of Classification Search
None
See application file for complete search history.

(56) References Cited

U.S. PATENT DOCUMENTS 8,772,580 B2 * 7/2014 Holland .................. A01H 5/12 435/410
9,139,846 B2 * 9/2015 Jansen ............... C12N 15/8286
9,700,012 B2 * 7/2017 Gibson .................... A01H 5/12

OTHER PUBLICATIONS

Liu et al., (1999). "First Report of Tomato Bushy Stunt Virus Isolated from Lettuce," Plant Disease, 83(3):101.
Nagata, R. T. (1992). "Clip and Wash Method of Emasculation for Lettuce," HortScience, 27(8):907-908.
Obermeier et al., (2001). "Characterization of Distinct Tombusviruses that Cause Diseases of Lettuce and Tomato in the Western United States," Phytopathology, 91(8):797-806.
Ryder et al., (1974). "Mist depollination of lettuce flowers," HortScience, 9:584.

* cited by examiner

*Primary Examiner* — Eileen B O Hara
(74) *Attorney, Agent, or Firm* — Morrison & Foerster LLP

(57) ABSTRACT

New lettuce variety designated 'PRO 1632' is described. 'PRO 1632' exhibits stability and uniformity.

17 Claims, No Drawings

LETTUCE VARIETY 'PRO 1632'

CROSS REFERENCE TO RELATED APPLICATION

This application claims the benefit under 35 § USC 119(e) of prior U.S. Provisional Patent Application No. 62/307,243, filed Mar. 11, 2016, the disclosure of which is hereby incorporated by reference in its entirety.

FIELD

This invention relates to the field of plant breeding. In particular, this invention relates to new lettuce, *Lactuca sativa*, variety 'PRO 1632'.

BACKGROUND

Lettuce is an increasingly popular crop. Worldwide lettuce consumption continues to increase. As a result of this demand, there is a continued need for new lettuce varieties. In particular, there is a need for improved green leaf and iceberg lettuce varieties that exhibit improved growth habits, bolting and tip burn tolerance, and disease resistance.

SUMMARY

In order to meet these needs, the present invention is directed to improved lettuce varieties.

In one embodiment, the present invention is directed to an improved iceberg lettuce variety that exhibits vigorous growth, increased weight and yield. In one embodiment, the present invention is directed to lettuce, *Lactuca sativa*, seed designated as 'PRO 1632' having ATCC Accession Number PTA-124209. In one embodiment, the present invention is directed to a *Lactuca sativa* lettuce plant and parts isolated therefrom produced by growing 'PRO 1632' lettuce seed. In another embodiment, the present invention is directed to a *Lactuca sativa* plant and parts isolated therefrom having all the physiological and morphological characteristics of a *Lactuca sativa* plant produced by growing 'PRO 1632' lettuce seed having ATCC Accession Number PTA-124209. In still another embodiment, the present invention is directed to an $F_1$ hybrid *Lactuca sativa* lettuce seed, plants grown from the seed, and a head isolated therefrom having 'PRO 1632' as a parent, where 'PRO 1632' is grown from 'PRO 1632' lettuce seed having ATCC Accession Number PTA-124209.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'PRO 1632' lettuce plants. In another embodiment, the present invention is further directed to tissue culture of 'PRO 1632' lettuce plants, and to lettuce plants regenerated from the tissue culture, where the plant has all of the morphological and physiological characteristics of 'PRO 1632' lettuce plants.

The present invention is further directed to a method of selecting lettuce plants by: a) growing more than one 'PRO 1632' lettuce plant, where the plants are grown from lettuce seed having ATCC Accession Number PTA-124209; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'PRO 1632' lettuce seed having ATCC Accession Number PTA-124209. In still another embodiment, the present invention is further directed to lettuce plants, lettuce parts from the lettuce plants (e.g., lettuce heads), and seeds produced therefrom where the lettuce plant is isolated by the breeding method of the invention.

DETAILED DESCRIPTION

Definitions

In order to more clearly understand the invention, the following definitions are provided:

Green Leaf Lettuce: Green leaf lettuce is *Lactuca sativa* L. The plant develops in an upright open growing habit with medium textured leaves. The leaves are typically somewhat savoyed, while the shape can vary by variety. Leaf margins are often undulated, lobed or frilled. Other leaves range in color from light green to dark green with a minimal midrib. Inner heart leaves are typically smaller and lighter green in color.

Iceberg Lettuce: Iceberg lettuce, *Lactuca sativa* L. var. *capitata* L. is also known as 'crisp head' lettuce. Iceberg lettuce is a lettuce plant type that forms a firm, spherical head formed with tightly folded brittle textured foliage. Internal color ranges from white to yellow to light green. The wrapper leaves surrounding the head are wider than they are long. Leaf margins can vary by type, being entire, undulating, or frilled. Wrapper leaf color ranges from yellow green to dark green.

Core Length: Core length is the length of the internal lettuce stem. Core length is measured from the base of the cut head to the tip of the core.

Core Diameter: Core diameter is the diameter of the lettuce stem at the base of the cut head.

Green Leaf Heart: Green leaf heart is the densest part of the Green Leaf plant, and is often yellow and light green in color and of succulent texture. The heart is generally enclosed by two to three outer darker green leaves.

Heart Length: Heart length is the length of the vertically sliced lettuce plant as measured from the base of the cut stem to the top leaf margin of the longest outermost leaf that encloses the green leaf heart.

Head Length: Core Length Ratio: The ratio of the head length to core length is indicative of the percentage of useable product produced by the lettuce plant.

Plant Diameter: The plant diameter is a measurement across the top of the lettuce plant at its widest point. The measurement of frame diameter is taken from the outer most leaf tip horizontally to the outer most leaf tip.

Head Diameter: Head diameter is the diameter of the vertically sliced lettuce plant head at its widest horizontal point, perpendicular to the stem.

Head Length: Head length is the diameter of the vertically sliced lettuce plant head as measured from the base of the cut stem to the cap leaf.

Average Head Diameter: Average head diameter is an average of the measured head diameter and head length of the lettuce head.

Average Head Diameter: Core Length Ratio: The ratio of the average head diameter to core length is indicative of the percentage of useable product produced by the lettuce plant.

Frame Diameter: The frame diameter is a measurement of the lettuce plant diameter at its widest point. The measurement of frame diameter is from the outer most wrapper leaf tip to outer most wrapper leaf tip.

Head Weight: Head weight is the weight of the marketable lettuce plant, cut and trimmed to market specifications.

Rogueing: Rogueing is the process in lettuce seed production where undesired plants are removed from a variety. The plants are removed because they differ physically from the general desired expressed characteristics of the variety. The differences can be related to size, color, maturity, leaf texture, leaf margins, growth habit, or any other characteristic that distinguishes the plant.

Market Stage: Market stage is the stage when a lettuce plant is ready for commercial lettuce harvest. In the case of a romaine lettuce variety, a romaine plant is at a marketable state when the heart has some density and the head has reached an adequate size and weight.

Tomato Bushy Stunt: Lettuce dieback was first observed in California in the mid-1980s, and reports of the disease have increased over the last 10 years. Complete crop losses have occurred in fields of Green Leaf lettuce, and no commercial Green Leaf cultivar has been shown to be resistant to the disease. In the U.S., Green Leaf is a rapidly growing market segment, having increased 68% over the last five years (USDA, 2002). The disease has occurred in commercial fields of some leaf lettuce cultivars; however, symptoms have never been observed on any modern crisphead (iceberg) cultivars. Lettuce dieback is caused by several related tombusviruses including tomato bushy stunt virus (TBSV) and lettuce necrotic stunt virus (LNSV) (Liu et al., 1999; Obermeier et al., 2001). These are soil-borne, highly stable, and mechanically transmitted, and have no known vector. The conditions affecting symptom development remain poorly understood. The disease is frequently observed in low-lying areas of fields with a prior history of flooding, suggesting that the virus may be carried in river water and/or that disease symptoms may be associated with increased root stresses such as those presented by excess moisture. No effective cultural or chemical control methods have yet been identified.

Resistance to Tomato Bushy Stunt refers to a level of resistance in a lettuce variety as measured by visual symptoms. Resistance is deemed present when symptoms are not present in at least 95% of a lettuce variety when exposed to tomato bushy stunt virus (TBSV).

Taking into account these definitions, the present invention is directed to seeds of the lettuce variety 'PRO 1632', plants produced by growing 'PRO 1632' lettuce seeds, heads isolated or harvested from the plants, one or more plants selected from a collection of 'PRO 1632' plants and seeds derived or produced therefrom; plants produced by crossing a lettuce plant with a 'PRO 1632' lettuce plant and seeds derived or produced therefrom.

Objective Description of the Variety 'PRO 1632'

'PRO 1632' is an iceberg lettuce variety that is larger heading, resistant to tip burn and bolting, and is suitable for plantings in regions such as the southern Salinas valley in California, and Yuma, Ariz.

Through extensive field trialing and screenings, 'PRO 1632' has demonstrated to have a large heading, resistance to tip burn and bolting, and to be well adapted for summer plantings in regions such as the southern Salinas valley, California and spring plantings in regions such as Yuma, Ariz.

'PRO 1632' was evaluated in multiple trials and evaluated for improved size, improved weight, improved frame size, and improved tolerances to tip burn and bolting.

As evaluated in multiple seed production fields and commercial plantings, 'PRO 1632' has been observed to be uniform and stable without variants.

As described herein, lettuce variety 'PRO 1632' has numerous distinguishing characteristics.

A. Variety Description Information

| | |
|---|---|
| Plant Type: | Iceberg |
| Seed: | |
| Seed Color: | Black |
| Light Dormancy: | No |
| Heat Dormancy: | Yes |
| Cotyledons: | |
| Shape of Cotyledons: | Intermediate |
| Shape of Fourth Leaf: | Spatulate |
| Length/Width Index of Fourth Leaf: | 26 |
| Apical Margin: | Moderately Dentate |
| Basal Margin: | Moderately Dentate |
| Undulation: | Medium |
| Green Color: | Medium |
| Anthocyanin: | Absent |
| Distribution: | None |
| Rolling: | Absent |
| Cupping: | Uncupped |
| Reflexing: | Slight |
| Mature Leaves: | |
| Margin: | |
| Incision Depth (Deepest penetration of the margin): | Moderate |
| Indentation (Finest Division of the Margin): | Crenate |
| Undulation of the Apical Margin: | Moderate |
| Green Color: | Medium |
| Anthocyanin | |
| Distribution: | None |
| Size: | Large |
| Glossiness: | Moderate |
| Blistering: | Slight |
| Leaf Thickness: | Thick |
| Trichomes: | Absent |

B. Comparison to Most Similar Variety

| Characteristic | PRO 1632 | PX 1565 |
|---|---|---|
| Spread of Frame Leaves | 42 cm | 35 cm |
| Head Diameter (market trimmed with single cup leaf) | 16 cm | 13 cm |
| Head Shape | Spherical | Spherical |
| Head Size Class | Large | medium |
| Head Count per Carton | 24 | 24 |
| Head Weight | 1030 | 840 |
| Head Firmness | Firm | Firm |
| Butt | | |
| Shape | Rounded | Rounded |
| Midrib | Flat | Flat |
| Core (Stem of Market-trimmed Head) | | |
| Diameter at the base of the Head | 3.0 cm | 4.0 cm |
| Ratio of Head Diameter/Core Diameter | 5.33 | 3.25 |
| Core Height from base of Head to Apex | 5.0 cm | 4.0 cm |
| Number of Days from First Water Date to Seed Stalk Emergence (Summer condition) | 75 | 71 |
| Bolting Class | Medium | Slow |
| Height of Mature Seed Stalk | 138 cm | 131 cm |
| Spread of Bolter Plant | 42 cm | 38 cm |
| Bolter Leaves | Curved | Curved |
| Margin | Dentate | Dentate |
| Color | Dark Green | Dark Green |
| Bolter Habit | | |
| Terminal Inflorescence | Present | Present |
| Lateral Shoots (above head) | Absent | Absent |
| Basal Side Shoots | Absent | Absent |
| Adaptation Regions | Salinas | Salinas |

-continued

| Characteristic | PRO 1632 | PX 1565 |
|---|---|---|
| | Valley, CA | Valley, CA Yuma, AZ. |

C. Growing Season

| Season | 'PRO 1632' | 'Salute' |
|---|---|---|
| Spring area | Salinas Valley, CA | Desert Southwest |
| Summer area | Salinas Valley, CA | Salinas Valley, CA |
| Fall area | Not Adapted | Not Adapted |
| Winter area: | Not Adapted | Not Adapted |

D. Diseases and Stress Reactions

| Disease or Stress | 'PRO 1632' | 'Salute' |
|---|---|---|
| Virus | | |
| Big Vein: | Susceptible | Susceptible |
| Lettuce Mosaic: | Susceptible | Susceptible |

E. Fungi/Bacteria

| Fungal/Bacterial | 'PRO 1632' | 'Laguna Fresca' |
|---|---|---|
| Corky Root Rot (Pythium Root Rot): | Susceptible | Susceptible |
| Downy Mildew (Races I, IIA, III): | Susceptible | Susceptible |
| Powdery Mildew: | Susceptible | Susceptible |
| Sclerotinia Rot: | Intermediate | Intermediate |
| Bacterial Soft Rot (*Pseudomonas* spp. & others): Not tested | Susceptible | Susceptible |
| Botrytis (Gray Mold): | Susceptible | Susceptible |
| Other: Corky Root Rot (*Rhizomonas suberifaciens*): | Susceptible | Susceptible |

F. Insects

| Insects | 'PRO 1632' | 'Laguna Fresca' |
|---|---|---|
| Cabbage Loopers: | Susceptible | Susceptible |
| Root Aphids: | Susceptible | Susceptible |
| Green Peach Aphid: | Susceptible | Susceptible |

G. Physiological/Stress

| Stress | 'PRO 1632' | 'Laguna Fresca' |
|---|---|---|
| Tipburn | Resistant | Resistant |
| Heat | Resistant | Resistant |
| Drought | Susceptible | Susceptible |
| Cold | Susceptible | Susceptible |
| Salt | Susceptible | Susceptible |

H. Post Harvest

| Characteristic | 'PRO 1632' | 'Laguna Fresca' |
|---|---|---|
| Pink Rib | Moderately Susceptible | Moderately Susceptible |
| Russet Spotting | Moderately Susceptible | Moderately Susceptible |
| Rusty Brown | Moderately Susceptible | Moderately Susceptible |
| Discoloration | | |
| Internal Rib Necrosis (Blackheart, Gray Rib, Gray Streak) | Moderately Susceptible | Moderately Susceptible |

Breeding and Selection

The present invention is further directed to the use of the 'PRO 1632' lettuce variety in breeding and selection of new varieties.

A. Breeding

In lettuce breeding, lines are selected for their appropriate characteristics. For example, one line may be selected for bolt tolerance in the fall growing conditions of the desert production locations of California and Arizona. Another line may be selected for the size, color, and texture of the lettuce head. Crosses are made, for example, to produce a dark green, sure heading iceberg lettuce with improved texture, and size for fall plantings in Yuma, Ariz. and Huron, Calif.

To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen is performed by procedures well known in the art of lettuce breeding.

The manual removal of anther tubes, though an effective means to ensure the removal of all self pollinating possibilities, is very tedious and time consuming when a large number of crosses are to be made. The breeders have therefore adapted a well documented and modified method of making crosses more efficiently using these methods. This particular cross was made by first misting the designated male flowers to wash the pollen off prior to fertilization. This process of misting is a proven and effective means of pollen removal that assures crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen is washed off with enough pressure to dislodge the pollen grains, but not enough to damage the style. Excess water is dried off with clean paper towels. About 30 minutes later, the styles should spring back up and the two lobes of the stigma are visibly open in a "V" shape. Pollen from another variety or donor parent is then introduced by gently rubbing the stigma and style of the donor parent to the maternal parent. Tags with the pertinent information on date and pedigree are then secured to the flowers in order to keep track.

About 2-3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two relevant references teaching methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907-908 both of which are hereby incorporated by reference in their entirety for the purpose of providing details on the techniques well known in the art.

B. Selection

In addition to crossing, selection may be used to identify and isolate new lettuce lines. In lettuce selection, lettuce seeds are planted, the plants are grown and single plant selections are made of plants with desired characteristics. Such characteristics may include improved head and frame size, deeper or darker green leaf color, etc. Seed from the single plant selections are harvested, separated from seeds of the other plants in the field and re-planted. The plants from the selected seed are monitored to determine if they exhibit the desired characteristics of the originally selected line. Selection work is continued over multiple generations to increase the uniformity of the new line.

Deposit Information

A deposit of the lettuce variety 'PRO 1632' is maintained by Progeny Advanced Genetics, having an address at 590A Works Street, Salinas, Calif. 93901, United States of America. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety made according to the Budapest Treaty in the American Type Culture Collection (ATCC), ATCC Patent Depository, 10801 University Boulevard, Manassas, Va., 20110, USA.

The lettuce variety 'PRO 1632' was deposited on Jun. 6, 2017 according to the Budapest Treaty in the American Type Culture Collection (ATCC), ATCC Patent Depository, 10801 University Boulevard, Manassas, Va., 20110, USA. The deposit has been assigned ATCC number PTA-124209. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the ATCC depository, which is a public depository, for a period of at least 30 years, or at least 5 years after the most recent request for a sample of the deposit, or for the effective life of the patent, whichever is longer, and will be replaced if a deposit becomes nonviable during that period.

This invention will be better understood by reference to the following non-limiting Examples.

EXAMPLES

Example 1: General Trialing Method

The following steps illustrate the general trialing method of the invention:

I. Set Up

1. A trial is set up to compare one or more lines. Parental lines and related varieties are identified.
2. Primary slots are identified.
3. Necessary accession lines are located and purchased/received from seed dealers or growers.
4. All varieties are assigned a number to maintain integrity and anonymity.
5. Trials are set up in with all necessary varieties. Variety arrangement for trial is diagramed.

II. Planting

1. Commercial plantings are located by contacting commercial growers during the planting slot recommended for the variety.
2. A field is located during commercial planting and the necessary rows and area is marked off.
3. Varieties are planted according to a diagram, generally in 100 foot ranges.
4. All varieties are planted in same manner to mimic the planting of the commercial variety as closely as possible.
5. A trial map is drawn diagramming the trial, the trial location in the field and directions to the field.

III. Maintenance

1. All varieties are treated identically. Plants are watered, fertilized, and treated to control pests in the same manner as other lettuce plants in the commercial field.
2. The trial is thinned to separate the plants for optimum growth.

IV. Evaluation

1. Evaluations are done as near to the time of the commercial harvest as possible.
2. The evaluation is conducted "blindly". The evaluator(s) do not have the key to the trial at the time of evaluation.
3. 24 heads of each variety are evaluated.
   a. The frame diameters of 24 random plants are measured to the nearest cm.
   b. 24 mature plants of each variety are cut to the cap leaf.
   c. The following measurements are then conducted and recorded:
      1. Each plant is weighed to the nearest gram.
      2. The core diameter of each head is measured to the nearest mm.
      3. The heads are then sliced in to halves, discarding 1 half
      4. The core lengths (from the cut stem to the core tip) are measured to the nearest mm.
      5. The plant length (from the cut stem to the cap leaf) is measured to the nearest mm.
      6. The plant diameter (at its widest point) is measured to the nearest mm.
      7. The heart length is measured to the nearest mm.
      8. The ideal maturity or harvest date is then estimated based on the solidity of the plant, the core length and any other physiological characteristics present.
      9. The leaf color is documented using the Munsell Color Charts for Plant Tissue.
   e. From these measurements, an Excel program is used to calculate the averages, the standard deviations and the T-Tests for the compared varieties.

Example 2: Comparative Analysis

Following the procedures of Example 1, 'PRO 1632' iceberg lettuce was compared to its closest variety, 'PX 1565'.

'PRO 1632' is a new and distinct variety of iceberg lettuce that most closely resembles the variety 'PX 1565'. 'PRO 1632' is a Salinas-type iceberg lettuce variety adapted to cooler lettuce production regions such as the Salinas valley of California. 'PRO 1632' is a larger heading and large framed variety, with excellent heading characteristics, head shape, and leaf texture. 'PRO 1632' is larger heading and framed than 'PX 1565', and has a black seed color, whereas 'PX 1565' is white.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

What is claimed:

1. A *Lactuca sativa* seed designated as 'PRO 1632', representative sample of seed having been deposited under ATCC Accession Number PTA-124209.

2. A *Lactuca sativa* plant produced by growing the seed of claim 1.

3. A plant part from the plant of claim 2.

4. The plant part of claim 3, wherein said part is a head, a leaf, or a portion thereof.

5. The plant part of claim 4, wherein said part is a head.

6. A *Lactuca sativa* plant having all the physiological and morphological characteristics of the *Lactuca sativa* plant of claim 2.

7. A plant part from the plant of claim 6.

8. The plant part of claim 7, wherein said part is a head, a leaf, or a portion thereof.

9. The plant part of claim 8, wherein said part is a head.

10. An $F_1$ hybrid *Lactuca sativa* plant having

'PRO 1632' as a parent where 'PRO 1632' is grown from the seed of claim 1.

11. A pollen grain or an ovule of the plant of claim 2.

12. A tissue culture of the plant of claim 2.

13. A lettuce plant regenerated from the tissue culture of claim 12, wherein the plant has all of the morphological and physiological characteristics of a lettuce plant produced by growing seed designated as 'PRO 1632', representative sample of seed having been deposited under ATCC Accession Number PTA-124209.

14. A method of making lettuce seeds, said method comprising crossing the plant of claim 2 with another lettuce plant and harvesting seed therefrom.

15. A method of selecting lettuce variety 'PRO 1632', comprising:

a. growing more than one plant from the seed of claim 1; and b. selecting a plant from step a).

16. A *Lactuca sativa* plant selected by the method of claim 15.

17. *Lactuca sativa* seed produced from the *Lactuca sativa* plant of claim 16.

* * * * *